United States Patent [19]

Murphy et al.

[11] Patent Number: 5,173,294

[45] Date of Patent: Dec. 22, 1992

[54] DNA PROBE FOR THE IDENTIFICATION OF HAEMOPHILUS INFLUENZAE

[75] Inventors: Timothy F. Murphy, Amherst; Michael A. Apicella, Pendleton, both of N.Y.

[73] Assignee: Research Foundation of State University of New York, Buffalo, N.Y.

[21] Appl. No.: 92,948

[22] Filed: Oct. 8, 1987

Related U.S. Application Data

[63] Continuation-in-part of Ser. No. 932,872, Nov. 18, 1986, abandoned.

[51] Int. Cl.⁵ .............................................. A61K 39/42
[52] U.S. Cl. .................................. 424/86; 435/320.1; 435/961; 435/972
[58] Field of Search ............... 424/86; 435/320.1, 961, 435/972

[56] References Cited

FOREIGN PATENT DOCUMENTS

87/03423 12/1987 PCT Int'l Appl. .

OTHER PUBLICATIONS

BA 81: 102075 1986.
BA 81: 72555 1986.
BA 82: 23820 1986.
BA 80: 40111 1985.
BA 79: 82898 1985.
BA 81: 4187 1985.
Murphy et al., "A Subtyping System For Nontypable Haemophilus Influenza Based on Outer-Membrane Proteins", J. Infect. Dis., 1983, 147:838–46.
Barenkamp et al., "Outer Membrane Protein and Biotype Analysis of Pathogenic Nontypable Haemophilus Influenzae" Infect. Immun., 1982, 36:535–40.
Loeb et al., "Outer Membrane Protein Composition in Disease Isolates of Haemophilus Influenzae, Pathogenic and Epidemiological Implications," Infect. Immun., 1980, 30:709–17.
Kennett, *Cell Fusion*, Methods Enzymol, 1979, 58:345–359.
Johnston, "Immunobiology of *Neisseria gonnorhoeae*", American Society for Microbiology, 1978, 121–9.
Westphal and Jann, "Bacterial Lipopolysaccharides", Methods in Carbohydrate Chemistry, 1965, 5:83–91.
Hitchock and Brown, Journal of Bacteriology, 1983 154:269–77.
Hansen et al., Immun. 1981, 32:1084–92.
Young & Davis, 1985, vol. 7, pp. 29–41.
Munson et al., "Purification and Comparison of Outer Membrane Protein P2 From Haemophilus Influenzae Type b Isolates," J. Clin. Invest., 1983, 72:677–684.
Munson et al., "Purification and Partial Characterization, of Outer Membrane Proteins P5 and P6 From *Haemophilus influenzae* Type b," Infection and Immunity, 1985, 49:544–549.

*Primary Examiner*—Paul J. Killos
*Attorney, Agent, or Firm*—Nixon, Hargrave, Devans & Doyle

[57] ABSTRACT

A plasmid which contains a genetic code for an immunogenic portion which is conserved in many strains of nontypable *Haemophilus influenzae* and the bacterium containing this plasmid is disclosed. The immunogenic portion is preferably an epitope on an outer membrane protein of *H. influenzae*. A monoclonal antibody to the immunogenic portion and the hybridoma which will produce the monoclonal antibody is also included. The invention further includes a DNA probe constructed to correspond to the nucleic acids which code for the immunogenic portion. This probe may be labelled with a radioactive marker and may be used as a diagnostic tool to assay various clinical samples for the presence of *H. influenzae*.

25 Claims, 5 Drawing Sheets

DNA PROBE FOR THE IDENTIFICATION OF HAEMOPHILUS INFLUENZAE

This application is a continuation-in-part of U.S. Ser. No. 932,872 filed Nov. 18, 1986, abandoned.

BACKGROUND OF THE INVENTION

*Haemophilus influenzae* type b has long been recognized as a frequent pathogen, particularly in infants and children, but only recently has nontypable *H. influenzae* been recognized as an important pathogen. It is now well established that nontypable *H. influenzae* causes pneumonia, bacteremia, meningitis, postpartum sepsis, and acute febrile tracheobronchitis in adults. In addition, nontypable *H. influenzae* causes neonatal sepsis and is a frequent etiologic agent in acute otitis media in infants and children. Therefore, the importance of discovering a method to assay a clinical sample such as sputum, cerebral spinal fluid, blood and others for the presence of *H. influenzae* is clear.

The observation that nontypable *H. influenzae* causes serious infections in adults and children has stimulated interest in study of the pathogenesis and potential virulence factors associated with this bacterium. The ribitol capsule of *H. influenzae* type b is a virulence factor for the organism, and antibody to capsule protects the host by means of bactericidal and/or opsonizing actions. These observations have generated much investigation on the role of the capsular polysaccharide in infection with *H. influenzae* type b and protection from these infections. However, nontypable *H. influenzae* lacks a polysaccharide capsule, and, similar to the outer membranes of other gram-negative bacteria, the outer membrane of *H. influenzae* is composed of outer membrane proteins (OMPs) and lipopolysaccharide (LPS). Therefore, studies of the relationship between virulence of nontypable *H. influenzae* and surface antigens focus on OMPs and LPS.

Analysis of OMPs of nontypable *H. influenzae* has shown that there are marked differences in OMP composition among strains. See e.g. Murphy et al, "A Subtyping System For Nontypable *Haemophilus influenzae* Based on Outer-membrane Proteins," J. Infect. Dis, 1983, 147:838–46; Barenkamp et al, "Outer Membrane Protein and Biotype Analysis of Pathogenic Nontypable *Haemophilus influenzae*," Infect. Immun, 1982, 36:535–40; Loeb et al, "Outer Membrane Protein Composition in Disease Isolates of *Haemophilus influenzae*, Pathogenic and Epidemiological Implications," Infect. Immun, 1980, 30:709–17.

A subtyping system for nontypable *H. influenzae* based on the major OMPs has previously been developed. If a surface exposed antigen (immunogen) which is conserved in all strains could be found, it would be an important tool in developing a method of identifying *H. influenzae* in clinical specimens as well as a vaccine against *H. influenzae*. It is therefore an object of this invention to find a surface exposed antigen in both typable and nontypable *H. influenzae* which is conserved in all strains including typable *H. influenzae* such as type b which is known to cause bacterial meningitis. It is a further object of this invention to develop a means for predictably identifying such conserved surface exposed antigen. It is a further object to develop a monoclonal antibody against such a surface exposed antigen. A further object of the invention is to develop a means for producing large quantities of such antigen and another object is to isolate and introduce the genetic sequence for such antigen into a novel plasmid and to cause expression of such sequence in a bacteria such as *E. coli* to produce such antigen.

Another object of the invention is to construct a nucleic acid probe through the combination of the surface exposed antigen in both typable and nontypable *H. influenzae* which is conserved in all strains and the monoclonal antibody which would be a diagnostic test for detecting *H. influenzae*.

BRIEF DESCRIPTION OF THE INVENTION

In accordance with the present invention there is provided a plasmid containing a genetic code for an immunogenic portion of a nontypable *Haemophilus influenzae*, which immunogenic portion is conserved in many strains of nontypable *H. influenzae*. The invention further includes a bacterium which contains said plasmid and will cause expression of said genetic sequence and includes a monoclonal antibody to the immunogenic portion and further includes the hybridoma which will produce said monoclonal antibody.

The immunogenic portion may be and preferably is an epitope on an outer membrane protein of the *H. influenzae* and specifically may be and preferably is a 16,600-dalton outer membrane protein. The DNA sequence for the gene expressing this 16,600-dalton outer membrane protein is believed to begin at nucleotide 125 and continues until nucleotide 526 of the cloned insert. The immunogenic portion may be produced in its pure state or as a part of a longer chain protein.

A diagnostic test for detecting *H. influenzae* in clinical samples comprises a nucleic acid probe synthesized to correspond to the nucleic acids which code for the immunogenic portion conserved in many strains of nontypable *H. influenzae*. This probe may be labelled, for example, with a radioactive or any other suitable diagnostically recognizable marker.

DETAILED DESCRIPTION OF THE INVENTION

"Nontypable *Haemophilus influenzae*" as used herein, means *H. influenzae* which lacks a polysaccharide capsule and which has an outer membrance comprising outer membrane proteins (OMPs) and also comprises lipopolysaccharides (LPS).

"Immunogenic portion" means that portion which will result in an immunological antibody response in a host organism. Such portion may be considered an antigen.

"Epitope" means that limited immunogenic portion which results in a specific immunological response.

In accordance with the present invention, a mouse monoclonal antibody that recognizes an epitope on a 16,600-dalton outer membrane protein (P6) was developed to nontypable *Haemophilus influenzae*. This epitope was present on all 115 isolates of *H. influenzae* tested, including typable and nontypable strains. Screening of 89 strains of other bacteria demonstrated that this epitope is a highly specific marker for *H. influenzae* because the epitope was absent in virtually all other bacterial species tested. Western blot assays were performed with two normal human serum samples and convalescent-phase serum from an adult with bacteremia due to nontypable *H. influenzae*. Antibody to the 16,600-dalton outer membrane protein was present in all three human serum samples.

Prototype strains of nontypable *H. influenzae* representing the eight OMP subtypes were obtained from our own collection. See Murphy et al, supra. Strain 3524 was isolated from the sputum of a patient with chronic bronchitis at the Erie County Medical Center (Buffalo, N.Y.). Dr. S. Berk (V.A. Medical Center, Mountain Home, Tenn.) provided 14 strains of nontypable *H. influenzae* from blood or transtracheal aspirates. The remaining strains of nontypable *H. influenzae* were clinical isolates from the Erie County Medical Center and the Buffalo V.A. Medical Center.

Dr. J. Ward (University of California at Los Angeles) provided 54 strains of *H. influenzae* type b. The remaining strains of *H. influenzae* type b were clinical isolates from the Buffalo Children's Hospital. Reference strains of other capsular serotypes of *H. influenzae* were obtained from the Centers for Disease Control (Atlanta).

Cultures of *Haemophilus paraphrophilus* ATCC 29240, *Haemophilus segnis* ATCC 10977, *Haemophilus parainfluenzae* ATCC 7901 and 9276, *Haemophilus aegypticus* ATCC 11116, *Haemophilus parahemolyticus* ATCC 10014, nontypable *H. influenzae* ATCC 19418, *Actinobacillus actinomycetemcomitans* ATCC 29522, ATCC 29523, ATCC 29524, NCTC 9707, and NCTC 9710, *Actinobacillus equili* ATCC 19392, *Actinobacillus seminis* ATCC 15768, and *Actinobacillus suis* ATCC 15557 were provided by Dr. J. Zambon (School of Dentistry, State University of New York at Buffalo). Isolates of all other species were provided by the clinical microbiology laboratory at the Erie County Medical Center.

The identity of strains of *H. influenzae* was confirmed by colonial morphology and growth requirement for hemin and nicotinamide adenine dinucleotide. Capsular serotypes were determined by CIE with use of reference strains and antiserum from the Centers for Disease Control, Murphy et al, supra. Strains were stored in Mueller-Hinton broth plus 10% glycerol at $-70°$ C.

BALB/c mice were immunized intraperitoneally with 0.1 ml of $10^9$ cells of nontypable *H. influenzae* strain 3524 on days 0 and 28. On day 32 after the initial immunization, selected animals were killed with chloroform, their spleens were removed, and splenic lymphocytes were harvested by perfusion of splenic pulp with minimal essential medium.

To achieve hybridoma development by fusion of the donor spleen cells to the NS 1 (nonsecreting variant of the IgG1 BA/c plasmacytoma P3XAg8) plasmacytoma cells (obtained from the Salk Institute of Biology [La Jolla, Calif.] under National Cancer Institute contract N01-CB-23886), 35% polyethylene glycol was used in a modification of the procedure of Kennett, Cell Fusion, Methods Enzymol, 1979, 58:345–359. In brief, $10^7$ spleen cells were combined with $10^6$ NS-1 cells in minimal essential medium with serum. The cells were centrifuged at 170 xg for 10 min at 25° C. All of the supernatant was removed, and the pellet was tapped to loosen it. Two-tenths milliliter of 35% polyethylene glycol 1,000 (Sigma Chemical Co., St. Louis) in minimal essential medium without serum was added and the mixture was stirred gently and left at 25° C. for 8 minutes, with the last 3 min consisting of centrifugation at 500 xg to pellet the cells. At the end of the original 8 minutes, 5 ml of minimum essential medium (MEM) with serum was added and gently pipetted once to resuspend the pellet. The mixture was centrifuged at 250 xg for 5 minutes at room temperature (25° C.). All of the supernatant was removed. Five milliliters of complete minimal essential medium (medium with glucose [4.5 mg/ml] and 20% fetal bovine serum) was added to resuspend the pellet. The mixture was transferred to a 25-ml Erlenmyer flask containing the appropriate amount of complete minimal essential medium to obtain $3 \times 10^5$ plasmacytoma cells/ml. The cells were stirred gently and distributed in 0.05-ml samples into microtiter wells.

At 24 hour after the polyethylene glycol fusion, 0.05 ml of medium containing hypoxanthine (13.6 $\mu$g/ml), aminopterin (0.36 $\mu$g/ml), and thymidine (3.87 $\mu$g/ml) was added to each well. The microtiter plates were placed in a tissue culture incubator at 85% humidity in an atmosphere of 5% $CO_2$ and 95% room air. Fresh medium containing hypoxanthine, aminopterin, and thymidine was added on day 7, and plates were checked for macroscopic plaques after day 10. The supernatant from all wells was tested for the presence of antibody with an ELISA (enzyme-linked immunosorbant absorbant assay).

ELISAs were performed in polyvinyl 96-well microtiter plates (Dynatech, Alexandria, Va.); 200-$\mu$l volumes were used for each step. Wells were coated with a cell envelope preparation (10 $\mu$g/ml) of nontypable *H. influenzae* strain 3524 prepared by the method of Johnston, "Immunobiology of *Neisseria gonorrhoeae*", American Society for Microbiology, 1978, 121–9. Plates were incubated at 37° C. for 1 hour followed by overnight incubation at 4° C. Wells were washed three times with PBS (phosphate buffered saline) plus 0.05% Tween 20 ® surfactant between each step. Unbound sites on the plastic were blocked with 3% bovine serum albumin in PBS for 2 hours at 37° C. Tissue culture supernatants (or dilutions of mouse ascites fluid in subsequent experiments) containing monoclonal antibody were incubated in the wells overnight at 4° C. Rabbit antibody to mouse IgG and IgM was then incubated for 2 hours at 37° C. followed by protein A-peroxidase for 2 hr at 37° C. Two hundred microliters of substrate was then added to each well. Substrate was prepared by dissolving 10 mg of o-phenyl-enediamine in 1 ml of methanol and adding this solution to 99 ml of citrate-phosphate buffer, pH 5.0, plus 0.1 ml of 3% $H_2O_2$. After the substrate was incubated for 45 min in the dark at room temperature, the reaction was stopped with 50 $\mu$l of 4N $H_2SO_4$. The $OD_{490}$ was measured. Each set of ELISAs was performed with a control in which NS-1 tissue culture supernatant or ascites fluid was used in place of the monoclonal antibody being tested. On the basis of the results of ELISA screening, selected clones were propagated by subsequent transfer to larger tissue culture wells. Large quantities of antibody were produced in tissue culture and by ip injection of $10^5$ hybridoma cells into pristane-primed BALB/c mice. The resulting ascitic fluid was harvested in three to four weeks and tested for specificity.

The strains to be assayed were grown on chocolate agar (or other appropriate medium, depending on the species) overnight at 37° C. in an atmosphere of 95% room air and 5% $CO_2$. Cells from one plate were harvested by suspension in PBS and centrifugation at 10,000 g for 20 minutes. The resulting pellet was suspended in enough PBS to allow the suspension to be drawn into a micropipette. One-tenth milliliter of the suspension of bacteria was added to 0.4 ml of sample buffer (0.06M Tris, 1.2% SDS, 1% B-mercaptoethanol, and 11.9% glycerol) and heated for 5 minutes in a boiling water bath. The resulting organisms are referred to as whole cell preparation.

A 10-μl drop of whole cell preparation was placed on a nitrocellulose sheet (Schleicher and Schuell, Inc., Keene, N.H.) and allowed to air-dry. The sheet was then placed in 3% gelatin in buffer A (0.012M Tris and 0.15M NaCl, pH 7.4) for 1 hour. After the sheet was rinsed with buffer A, it was placed in an appropriate dilution of antibody and allowed to shake at room temperature overnight. The sheet was rinsed with buffer A and placed in 1:3,000 dilution of protein A peroxidase (Zymed Laboratories, San Francisco) and shaken for 1 hour at room temperature. The sheet was rinsed and immersed in horseradish peroxidase color development solution (0.015% $H_2O_2$; Bio-Rad, Richmond, Calif.) for 45 minutes. Controls assayed on each sheet included sample buffer (negative control). A negative result was recorded when the dot was no different from the background color, and a positive result was recorded when the dot turned purple-blue. About 90% of dot assays were unequivocally positive or negative. Those strains that yielded equivocal results in the dot assay were subjected to Western blot assay.

Preparation of LPS. Lipopolysaccharide (LPS) was prepared from nontypable *H. influenzae* strain 3524 by two methods. The first method was a modification of the phenol-water extraction method of Westphal and Jann, "Bacterial Lipopolysaccharides", Methods in Carbohydrate Chemistry, 1965, 5:83–91. The second method was that of Hitchcock and Brown, Journal of Bacteriology, 1983, 154:269-77. The latter method uses the enzyme proteinase K (Boehringer Mannheim GmbH, Mannheim, Federal Republic of Germany), which hydrolyzes proteins but has no effect on LPS.

Whole cell and LPS preparations were subjected to SDS-PAGE (sodium dodecyl sulfate polyacrylamide gel electrophoresis) with either 11% or 13.2% separating gels, Murphy et al, supra. When electrophoresis was completed, the gel was placed with a nitrocellulose sheet that had been previously boiled in distilled water, and the sheet was immersed in 0.3M sodium citrate plus 3M NaCl. Electrophoretic transfer was carried out in a Trans-Blot® cell (Bio-Rad) at 50 V for 90 minutes. The electrode buffer was 0.025M Tris, pH 8.3, 0.192 M glycine, and 20% methanol. The nitrocellulose sheet was then treated exactly as described for the dot assay; it was blocked with 3% gelatin and incubated sequentially with antibody 7F3, protein A-peroxidase, and substrate horseradish peroxidase color developer.

I radiolabeling of surface OMPs. Extrinsic labeling of surface-exposed OMPs was accomplished with a lactoperoxidase-catalyzed radioiodination procedure, Hansen et al, Infect. Immun. 1981, 32:1084–92.

Figure 1:
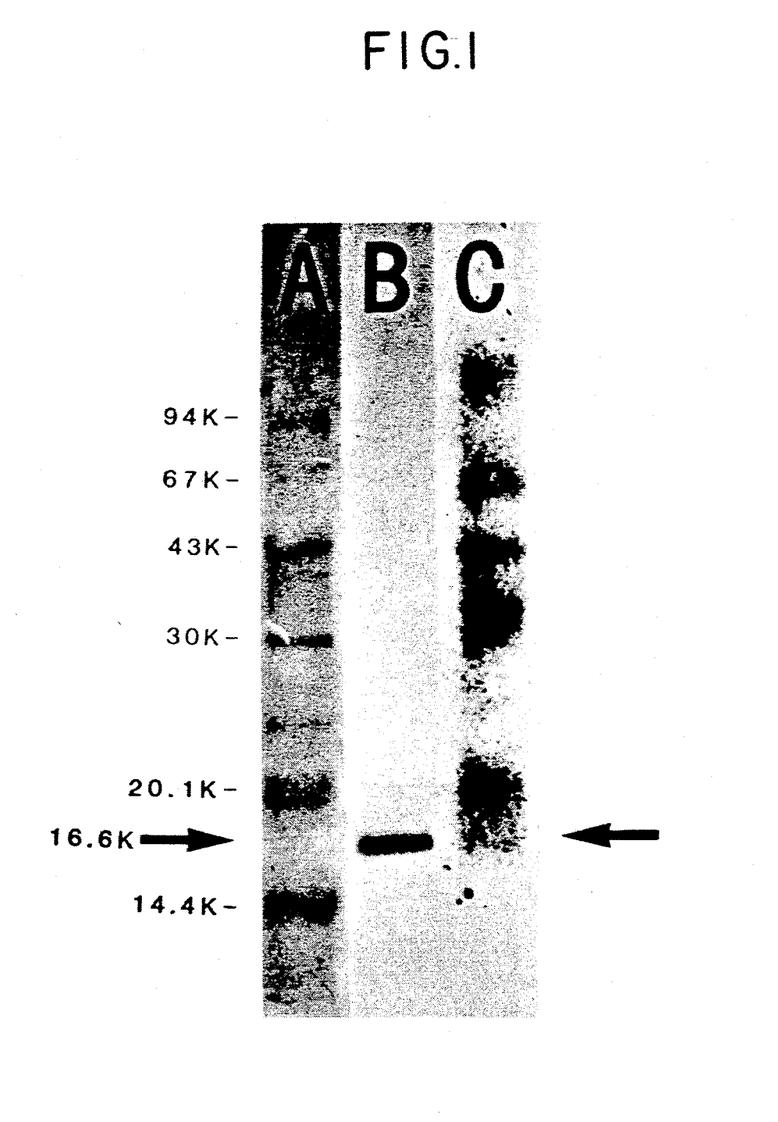

The ELISA with outer membranes of nontypable *H. influenzae* strain 3524 coated on microtiter plates demonstrated that the hybridoma designated 7F3 was producing antibody 7F3 that recognized a determinant in the outer membrane of the bacterium. Gel immunodiffusion indicated that this antibody was of the IgG3 isotype. FIG. 1 shows a Western blot that indicates that the determinant recognized by antibody 7F3 was on a protein with a molecular size of 16,600 daltons; lane A shows molecular weight standards on the nitrocellulose sheet, and lane B shows the 16,600-dalton protein recognized by antibody 7F3 in a whole cell preparation of nontypable *H. influenzae* strain 3524. Specifically, lane A shows molecular weight standards transferred from a 13.2% gel; lane B shows a whole cell preparation of nontypable *H. influenzae* strain 3524 incubated with antibody 7F3, protein A-peroxidase, and peroxide substrate; and lane C is an autoradiograph of a whole cell preparation of nontypable *H. influenzae* strain 3524 made from bacteria extrinsically labeled with $^{125}$I. All three lanes were from the same gel. Western blot assay done by this method in 25 strains of *H. influenzae* showed that antibody 7F3 recognized a determinant on this 16,600-dalton protein in every strain. Because the antibody recognized a determinant on a protein of identical molecular size in multiple strains, we screened larger numbers of strains with use of a dot assay rather than Western blot.

To determine whether the protein recognized by antibody 7F3 could be extrinsically labeled, we labeled nontypable *H. influenzae* strain 3524 with $^{125}$I. The proteins were subjected to SDS-PAGE and transferred to a nitrocellulose sheet. One lane was exposed to x-ray film, and one lane was incubated with 7F3, protein A-peroxidase conjugate, and substrate. FIG. 1 shows that the band recognized by antibody 7F3 (lane B) corresponds to an $^{125}$I-labeled band (lane C).

To assess further whether the epitope recognized by antibody 7F3 was on a protein or on LPS, we performed two additional experiments. An ELISA was performed as described above in which some wells were coated with a cell envelope preparation of nontypable *H. influenzae* strain 3524 and other wells were coated with LPS prepared from nontypable *H. influenzae* strain 3524 by the phenol-water method Westphal et al, supra. Antibody 7F3 was reactive with a cell envelope preparation (OD, 0.375) that contained OMPs and LPS, Johnston et al, supra, but was nonreactive with LPS (OD, 0.062). This finding indicates that the epitope recognized by antibody 7F3 resides on an OMP.

Figure 2:
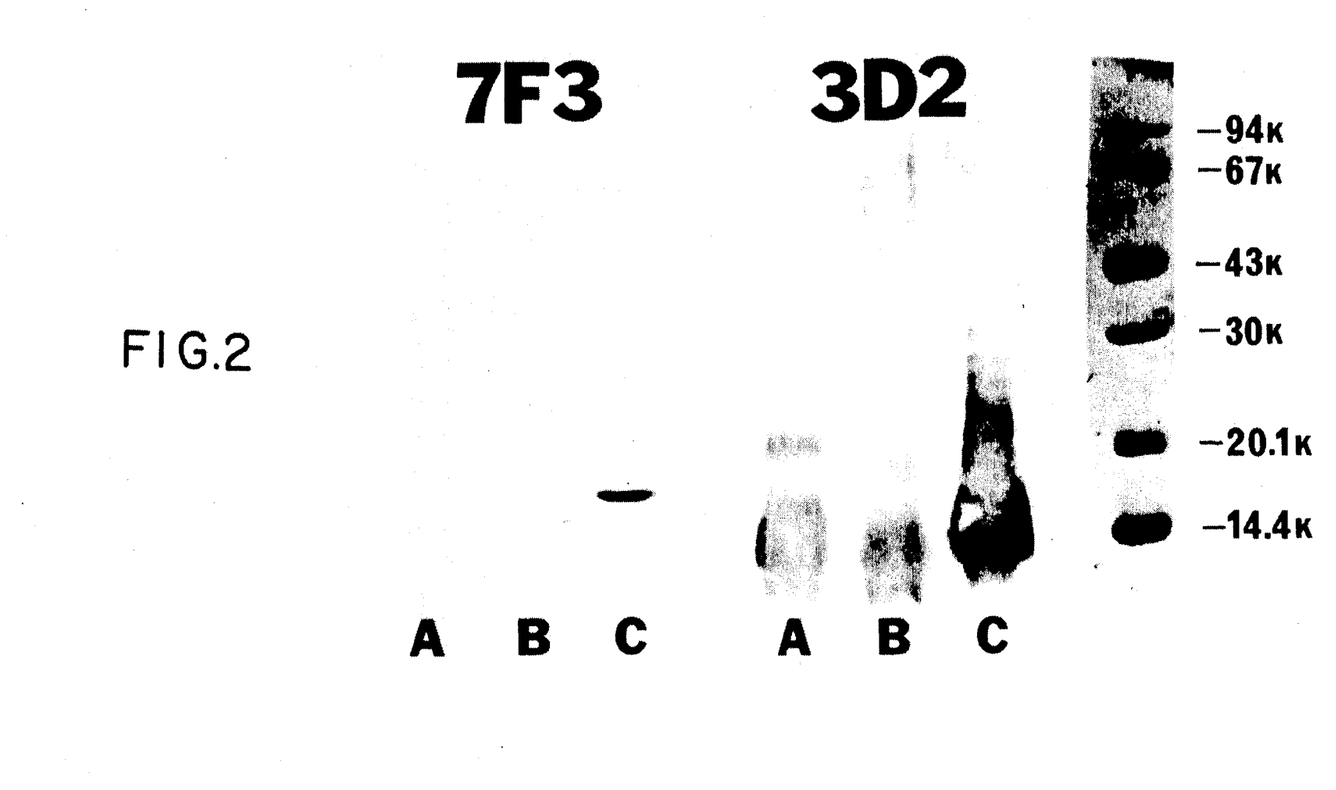

FIG. 2 is a Western blot assay depicting another experiment designed to assess whether the epitope recognized by antibody 7F3 is on a protein or LPS. The lanes marked A contain LPS prepared by proteinase K lysis of cells of strain 3524, (method of Hitchcock et al., J. Bacteriol, 1983, 154:269-77). The lanes marked D contains LPS of strain 3524 prepared by the phenol-water method, Westphal et al, supra, and the lanes marked C contain a whole cell preparation of strain 3524. All samples were assayed on the same gel and transferred to the same nitrocellulose sheet. FIG. 2, left, was incubated with antibody 7F3 (ascites fluid dilution, 1:500), and FIG. 2, right, was incubated with antibody 3D2 (ascites fluid dilution, 1:500), a monoclonal antibody that recognizes the lipid A portion of *H. influenzae* LPS. Antibody 7F3 does not bind to either of the LPS preparations and binds only to a band with a molecular weight of 16,600 daltons in the whole cell preparation. This observation demonstrates that antibody 7F3 recognizes an epitope on a protein and not on LPS.

Specifically, FIG. 2 shows a Western blot assay from a 13.2% gel: (left) incubation with antibody 7F3 and (right) incubation with antibody 3D2, which recognizes an epitope on the lipid A of *H. influenzae*. The lanes marked A contain LPS of nontypable *H. influenzae* strain 3524 prepared by lysis of cells with proteinase K, the lanes marked B contain phenol-water prepared LPS of strain 3524, and the lanes marked C contain a whole cell preparation of strain 3524. Molecular weight standards are noted on the right.

Studies were performed to determine the species specificity of the antigen recognized by antibody 7F3. Whole cell preparations of 115 isolates of *H. influenzae* were studied by either dot assay or Western blot assay. The strains included 73 type b, 37 nontypable, and 1 each of types a and c-f. All 115 strains of *H. influenzae* contained the epitope recognized by antibody 7F3, a result indicating that this epitope is a common antigen among strains of *H. influenzae*.

Sixty isolates of various bacterial species were studied to determine whether this epitope is present in bacteria other than *H. influenzae*. All 60 of these strains lacked the determinant recognized by antibody 7F3 (Table 1).

TABLE 1

SPECIFICITY OF ANTIBODY 7F3 FOR VARIOUS BACTERIAL SPECIES

| Bacterium | No. tested | No. positive |
|---|---|---|
| Gram-negative | | |
| *Escherichia coli* | 10 | 0 |
| *Actinobacillus* species | 10 | 0 |
| *Proteus* species | 7 | 0 |
| *Pseudomonas* species | 5 | 0 |
| *Klebsiella* species | 4 | 0 |
| *Serratia* species | 4 | 0 |
| *Enterobacter cloacae* | 1 | 0 |
| *Morganella morganii* | 1 | 0 |
| *Neisseria gonorrhoeae* | 6 | 0 |
| *Neisseria* species | 2 | 0 |
| Gram-positive | | |
| *Staphylococcus aureus* | 5 | 0 |
| *Staphylococcus* species | 2 | 0 |
| *Viridans streptococci* | 1 | 0 |
| *Streptococcus faecalis* | 1 | 0 |
| Diphtheroids | 1 | 0 |
| Total | 60 | 0 |

Twenty-nine strains of Haemophilus species other than *H. influenzae* were studied. Twenty-five of these isolates lacked the 7F3 epitope (Table 2). Two strains of *H. parahemolyticus* contained the determinant. In addition, one strain of *H. paraphrophilus* and one of *H. aegypticus* contained a 20,000-dalton protein that was recognized by antibody 7F3.

TABLE 2

SPECIFICITY OF ANTIBODY 7F3 FOR VARIOUS SPECIES OF HAEMOPHILUS

| Species | No. tested | No. positive |
|---|---|---|
| *H. parainfluenzae* | 24 | 0 |
| *H. parahemolyticus* | 2 | 2 |
| *H. paraphrophilus* | 1 | 1* |
| *H. segnis* | 1 | 0 |
| *H. aegypticus* | 1 | 1* |
| Total | 29 | 4 |

*In the Western blot assay, antibody 7F3 recognized a 20,000-dalton protein in these strains.

Figure 3:
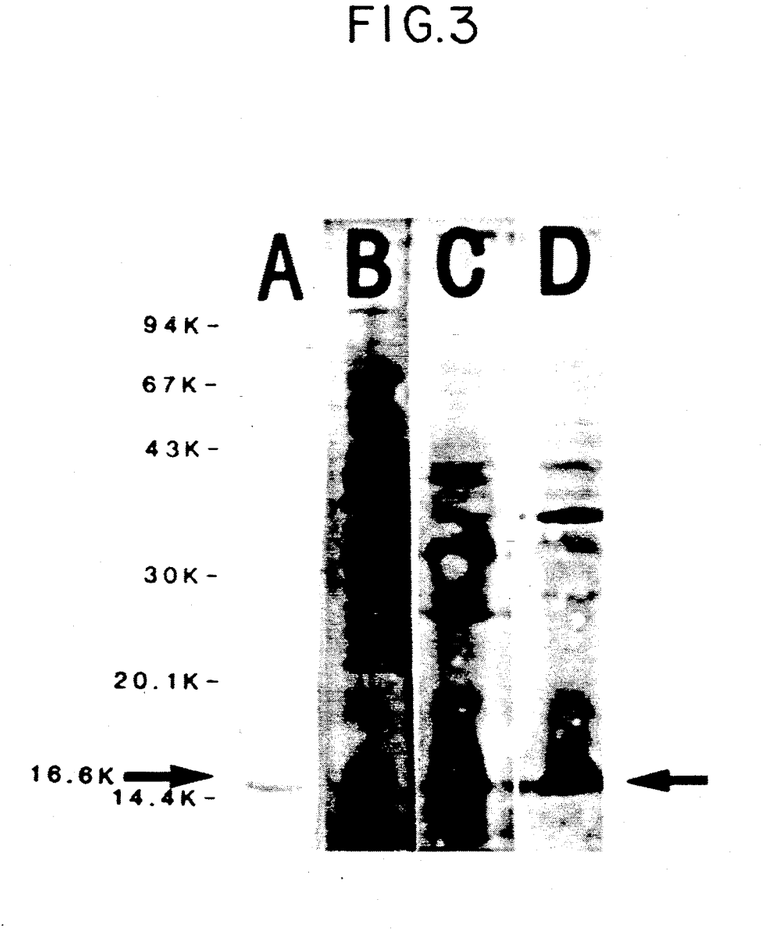

Human serum antibody. Human serum was tested for the presence of antibody to the 16,600-dalton OMP by Western blot assay. FIG. 3 shows whole cell preparations of nontypable *H. influenzae* strain 3524 that were assayed on the same gel and transferred to nitrocellulose paper; lane A was incubated with 7F3 ascites fluid and shows a single band corresponding to the 16,600-dalton protein, lanes B and C were incubated with two different samples of normal human serum, and lane D was incubated with serum obtained from an adult 17 days after bacteremia due to nontypable *H. influenzae*. All three samples of human serum have antibody to the 16,600-dalton OMP that contains the determinant recognized by antibody 7F3.

The DNA sequence for the gene encoding this 16,600-dalton outer membrane protein is believed to begin at nucleotide 125 of the insert and continues until nucleotide 526 as shown in Table 3(b). The deduced amino acid sequence is also included (Table 3(b)). The sequence of the 857bp insert containing the gene has the following sequence as shown in Table 3(b):

TABLE 3

Restriction Map

Amino Acid
DNA Sequence (b) CCCAAG<u>TAAAAT</u>TTCCAGCTTGGTCTCCATACTTAACTAAATAAAAAACTCATTT<u>AGGAG</u>AAATCTA
1

```
    met asn lys phe val lys ser leu leu val ala gly ser val ala ala leu
    ATG AAC AAA TTT GTT AAA TCA TTA TTA GTT GCA GGT TCT GTA GCT GCA TTA
    68                                                                100 ala ala  | cys ser ser ser asn asn asp ala ala gly asn gly ala ala gln
    GCG GCT  | TGT AGT TCC TCT AAC AAC GAT GCT GCA GGC AAT GGT GCT GCT CAA
             125 thr phe gly gly tyr ser val ala asp leu gln gln arg tyr asn thr val
    ACT TTT GGC GGA TAC TCT GTT GCT GAT CTT CAA CAA CGT TAC AAC ACC GTA
                                                 200 tyr phe gly phe asp lys tyr asp ile thr gly glu tyr val gln ile leu
    TAT TTT GGT TTT GAT AAA TAC GAC ATC ACC GGT GAA TAC GTT CAA ATC TTA asp ala his ala ala tyr leu asn ala thr pro ala ala lys val leu val
    GAT GCG CAC GCA GCA TAT TTA AAT GCA ACG CCA GCT GCT AAA GTA TTA GTA
                                   300
```

TABLE 3-continued

| glu | gly | asn | thr | asp | glu | arg | gly | thr | pro | glu | tyr | asn | ile | ala | leu | gly |
|-----|-----|-----|-----|-----|-----|-----|-----|-----|-----|-----|-----|-----|-----|-----|-----|-----|
| GAA | GGT | AAT | ACT | GAT | GAA | CGT | GGT | ACA | CCA | GAA | TAC | AAC | ATC | GCA | TTA | GGA |

| gln | arg | arg | ala | asp | ala | val | lys | gly | tyr | leu | ala | gly | lys | gly | val | asp |
|-----|-----|-----|-----|-----|-----|-----|-----|-----|-----|-----|-----|-----|-----|-----|-----|-----|
| CAA | CGT | CGT | GCA | GAT | GCA | GTT | AAA | GGT | TAT | TTA | GCA | GGT | AAA | GGT | GTT | GAT |

400

| ala | gly | lys | leu | gly | thr | val | ser | tyr | gly | glu | glu | lys | pro | ala | val | leu |
|-----|-----|-----|-----|-----|-----|-----|-----|-----|-----|-----|-----|-----|-----|-----|-----|-----|
| GCT | GGT | AAA | TTA | GGC | ACA | GTA | TCT | TAC | GGT | GAA | GAA | AAA | CCT | GCA | GTA | TTA |

| gly | his | asp | glu | ala | ala | tyr | ser | lys | asn | arg | arg | ala | val | leu | ala | tyr |
|-----|-----|-----|-----|-----|-----|-----|-----|-----|-----|-----|-----|-----|-----|-----|-----|-----|
| GGT | CAC | GAT | GAA | GCT | GCA | TAT | TCT | AAA | AAC | CGT | CGT | GCA | GTG | TTA | GCG | TAC |

500 termination

TAA TTCTTGGTATTTCTAATACTTGAAAAACAGGATCCATTTTTTATTGGATCCTGTTTTGTTTTC

ATCGTTTGTAATTTAACCAATTAGCTTGAAAGAATGAATTTATTCTTTTGATTCTAAAATAAATGCG

600

TTATCATTAACTCATCAACACAGTGGGTCGTTAGCTCAGTCGGTAGAGCAGCGGACTTTTAATCCGT

700

TGGTCGAAGGTTCGAATCCTTCACGACCCACCACTCTCTGATTTAATTGTCCAGTTGGGTTGTTAGCT

CAGTTGGTAGAGCAGCGGACTCTTAATTCGTCGGTCGAGAGTTCGAGCCTCTCACAACCTACCATTCT

800

TACCG

---

It is worthy of note that this band is among the most prominent recognized by antibody in human serum.

Specifically, FIG. 3 shows a Western blot assay from a 13.2% gel. All four lanes contain a whole cell preparation of nontypable H. influenzae strain 3524 from the same gel, but each lane was incubated with a different antiserum: lane A, antibody 7F3; lanes B and C, two different samples of normal human serum (dilution, 1:500); and lane D, serum obtained 17 days after bacteremia due to nontypable H. influenzae in an adult (dilution, 1:500). The incubation with antiserum was followed by incubation with protein A-peroxidase and peroxide substrate. The arrows indicate that all three samples of human serum contain antibody to the 16,600-dalton OMP that contains the 7F3 epitope. Molecular weight standards are indicated on the left.

In accordance with the invention, an IgG3 mouse monoclonal antibody that recognizes an epitope on a 16,600-dalton OMP on the surface of nontypable H. influenzae has been developed. This epitope is present in all 115 isolates of H. influenzae tested, including typable and nontypable strains. Screening of 60 strains of non-Haemophilus species demonstrated that the epitope is absent in all of these bacteria. The epitope was absent in 24 strains of H. parainfluenzae but was present in four to five strains of other Haemophilus species (Table 2). These species are unusual pathogens in humans. Therefore, from the standpoint of clinically relevant isolates, antibody 7F3 is highly specific for H. influenzae.

This monoclonal antibody recognizing a common epitope that is highly specific for H. influenzae can be useful as a tool in the clinical microbiology laboratory. A rapid test to confirm the identity of a clinical isolate as H. influenzae (typable or nontypable) could be developed based on such an antibody. In order to synthesize a nucleic acid probe to exploit this specific epitope, the DNA sequence of the gene encoding P6 is determined. Based on the DNA sequence, the amino acid sequence of the P6 protein can be deduced. This information can be used to perform what is known as epitope mapping.

Epitope mapping involves the construction of a number of small peptides and testing these peptides for reactivity with monoclonal antibody 7F3. Since the eptitope recognized by 7F3 is specific for H. influenzae, the corresponding peptide recognized by that antibody represents the specific determinant on H. influenzae. Once the amino acid sequence of the peptide is known, the DNA sequence of that segment can be deduced. Since H. influenzae contains the gene which codes for this epitope, the bacterium is known to contain DNA which has a sequence corresponding to this sequence. A nucleic acid probe can, therefore, be synthesized to correspond to the nucleic acids which code for the specific epitope on P6. Once the probe is synthesized, it can be labelled, for example, with a radioactive or other diagnostically recognizable marker. This probe could then be used to assay a clinical sample such as sputum, cerebral spinal fluid, blood and others for the presence of H. influenzae. This will be possible because the nucleic acid probe will bind to its complementary base pairs which are present in the genome of H. influenzae. Once this probe is synthesized, this approach would represent an advantage over the current, widely used method of demonstrating growth requirements for hemin and nicotinamide adenine dinucleotide. An assay utilizing a specific monoclonal antibody, or a specific nucleic acid probe, can reduce the time required for detection or identification of Haemophilus influenzae.

OMPs and LPS are closely associated on the outer membranes of gram-negative bacteria. This fact and the observation that the determinant recognized by antibody 7F3 is in the molecular weight range where LPS separates lead one to question whether this determinant is on a protein or on LPS. Several lines of evidence indicate that the epitope recognized by antibody 7F3 is on a protein. First, staining with Coomassie blue of SDS gels demonstrated the presence of a band recognized by antibody 7F3 at 16,600 daltons in all strains of *H. influenzae*. Because Coomassie blue stains protein but not LPS, this observation is presumptive evidence that antibody 7F3 recognizes a protein determinant. Second, the configuration of the band on SDS-PAGE and Western blot was typical for protein; LPS showed multiple bands that were generally less distinct than the band at which the antibody 7F3 epitope resides. This point is further corroborated by the observation that monoclonal antibodies that recognize LPS determinants showed the typical "LPS" pattern in Western blot assays of whole cell preparations, in contrast to the well-defined single band recognized by antibody 7F3. Third, by ELISA, antibody 7F3 showed reactivity with cell envelope preparations that contain OMPs plus LPS, but the antibody showed no reactivity with isolated LPS. Finally, in the Western blot assay (FIG. 2), antibody 7F3 recognized a band in a whole cell preparation but failed to recognize determinants on LPS that was prepared by using two different methods. Taken together, these observations indicate that the epitope recognized by antibody 7F3 resides on an OMP.

To assess whether the OMP containing the antibody 7F3 epitope was surface exposed, OMPs were labeled by using a lactoperoxidase-catalyzed radioiodination procedure, Hansen et al, supra. FIG. 1 shows that the protein containing the antibody 7F3 epitope is radiolabeled. This observation suggests that this 16,600-dalton OMP is surface exposed. For the purposes herein "surface exposed" or "outer membrane" means available for antibody binding.

The OMPs of nontypable *H. influenzae* show substantial strain-to-strain variability, as demonstrated by SDS-PAGE analysis. This variability in the major OMPs in the 32,000–42,000-dalton range is the basis of the subtyping system for nontypable *H. influenzae*, Murphy et al, supra. It is of interest that studies of OMPs of *H. influenzae* from three laboratories have independently noted the presence of a "16,000"-dalton OMP in all strains of *H. influenzae* studied, Murphy et al, Barenkamp et al and Loeb et al, supra. It is this protein that contains the antigenic determinant recognized by antibody 7F3. The present study indicates that the epitope recognized by antibody 7F3 on this low-molecular-weight OMP is an antigen common to all strains of *H. influenzae*. Identifying common surface antigens among strains is useful from the point of view of vaccine development because immunization with a single common antigen might induce protection from disease due to many strains. In addition, the observation that this 16,600-dalton protein has varied far less than other OMPs in the course of evolution leads to the speculation that this protein serves an important function for the bacterium and that its function is closely related to conservation of its structure.

The outer membranes of gram-negative bacteria are immunologically important structures because of their accessibility to host defense mechanisms. Indeed, antibody to OMPs of *H. influenzae* type b are widely prevalent in adults and are detected in the serum of infants who are convalescing from infections with *H. influenzae*. It has now been demonstrated that antibody to a 16,600-dalton OMP (P6) is present in human serum (FIG. 3). The presence of antibody to this OMP in normal human serum suggests that the OMP is important with regard to the human antibody response to *H. influenzae*.

Several observations suggest that P6 is an important target in immunity to *Haemophilus influenzae*:

1) Antibody raised from P6 isolated from a type b strain protects in an infant rat model.

2) A monoclonal antibody, 7F3, directed against P6 blocks human bactericidal activity against *Haemophilus influenzae* (NtHi).

3) Depleting normal human sera of P6 by affinity chromatography resulted in reduced bactericidal activity of that sera for *Haemophilus influenzae*.

4) And, immunopurified antibody to P6 from human sera was bactericidal.

This invention therefore includes the molecular cloning of P6 using *H. influenzae* as a source of bacterial chromosomal DNA, lambda gt11 bacteriophage as the vector in construction of the genomic library, pUC18 plasmid as the vector used in subcloning the gene to facilitate sequencing, and *E. coli* as the host strains. The results allow further analysis of the molecular basis of both experimental and human immunity to P6 and permits large quantities of P6 to be produced once it is approved for use in vaccine against *Haemophilus influenzae*.

Molecular Cloning of P6

The 16,600 dalton protein, designated herein as P6, is therefore present in the outer membranes of both typable and nontypable strains of *Haemophilus influenzae* and may be an important target in immunity to *Haemophilus influenzae*. The DNA sequence for the gene encoding this 16,600-dalton outer membrane protein is believed to begin at nucleotide 125 and continues until nucleotide 526of Table 3(b). In accordance with this invention P6 is cloned molecularly using a nontypable strain of *Haemophilus influenzae* as a source of bacterial chromosomal DNA, lambda gt11 bacteriophage as the vector in construction of the genomic library, pUC 18 plasmid as the vector in subcloning the gene to facilitate sequencing, and *E. coli* as the host strain. The monoclonal antibodies previously discussed and a polyclonal antiserum were used to screen for expression of P6. A portion of the genomic library was screened resulting in the detection of four positive recombinants. One, clone O, appears to produce a full length gene product expressed in high frequency. The DNA insert of this clone was used to subclone the gene into a plasmid vector. An *E. coli* transformant, 7-9B, also appears to express a full length gene product. It is likely that transcription is initiated from the actual promoter of the P6 gene, since both clone O and transformant 7-9B express the gene product in both the uninduced and induced states. Isolating and sequencing the gene for P6 allows for further analysis of the molecular basis of both experimental and human immunity to Bp6.

More specifically, recombinent DNA techology was used to clone the gene for the 16,600 dalton surface protein, P6, of nontypable *Haemophilus influenzae* (NtHi) into *Escherichia coli*. Chromosomal DNA from a clinical isolate was sheared, ligated to lambda gt11 arms and packaged into phage heads. Four recombinant phages were detected by screening with monoclonal antibodies and a polyclonal antiserum. One, clone O, was restricted with EcoRI and ligated to plasmid vector pUC18 to facilitate sequencing. *E. coli* carrying recombinant plasmids were screened resulting in one positive, 7-9B. Both clone O and 7-9B produce a protein with an apparent molecular weight equal to or similar to native P6 as determined by Western blot analyses. In screening it was determined that transcription and translation of the *Haemophilus influenzae* P6 gene(s) were not dependent on the lac operator and promoter of either vector. Using immunofluorescence, the recombinant gene product's P6 epitopes could be localized on the surface of these *E. coli* and accessible to antibody.

*Haemophilus influenzae* strain 1479 was grown at 37 degrees C. in brain heart infusion broth supplemented with heme (10 μg/ml) and nicotinamide adenine dinucleotide (10 μg/ml).

The *E. coli* strain y1090 (r−m+) was used for the lytic growth of bacteriophage lambda gt11 and strain JM83 as the host for the plamid pUC18. The *E. coli* strains were grown in L-broth (LB) or on LB agar with or without 50 μg/ml of ampicillin, depending on the host strain. A more detailed description for the use of the respective host strains can be found elsewhere. Young et al, Science 222: 778–782; Messing Rec. DNA Tech. Bull. 2:43–48.

A pellet of *Haemophilus influenzae* 1479 cells from a 750 ml culture was resuspended in 10 mls of 10 mM HEPES buffer, pH 7.4. To this mixture was added EDTA to a concentration of 5 mM and SDS to a concentration of 0.5% w/v and then incubated at 60 degrees C. for 30 minutes. This lysate was then digested with 0.5 ml of pronase (10 mg/ml) at 37 degrees C. for 2 hours and then subjected to two phenol/CIAA extractions followed by one chloroform, isoamyl alcohol, 24:1 (CIAA) extraction. Sodium chloride was added to a concentration of 0.2M to the aqueous phase, and DNA was precipitated with 2.5 volumes of chilled ethanol. Following precipitation in the cold, the DNA was pelleted by centrifugation, resuspended in Tris-EDTA buffer, and treated with DNase-free RNase at a concentration of 0.1 mg/ml at 37 degrees C. for 1 hour. Finally, the DNA was extracted with phenol/CIAA, precipitated with sodium chloride and ethanol, and pelleted by centrifugation. The DNA was resuspended in Tris-EDTA buffer, measured for concentration by $A_{260}/A_{280}$ and stored at 4 degrees C.

The phage library was screened with monoclonal antibody 7F3. Also used in screening was rabbit polyclonal antiserum produced by immunizations with solubilized P6 preparations of *Haemophilus influenzae* strain 1808.

Construction of the *Haemophilus influenza* 1479 genomic library

Figure 4:
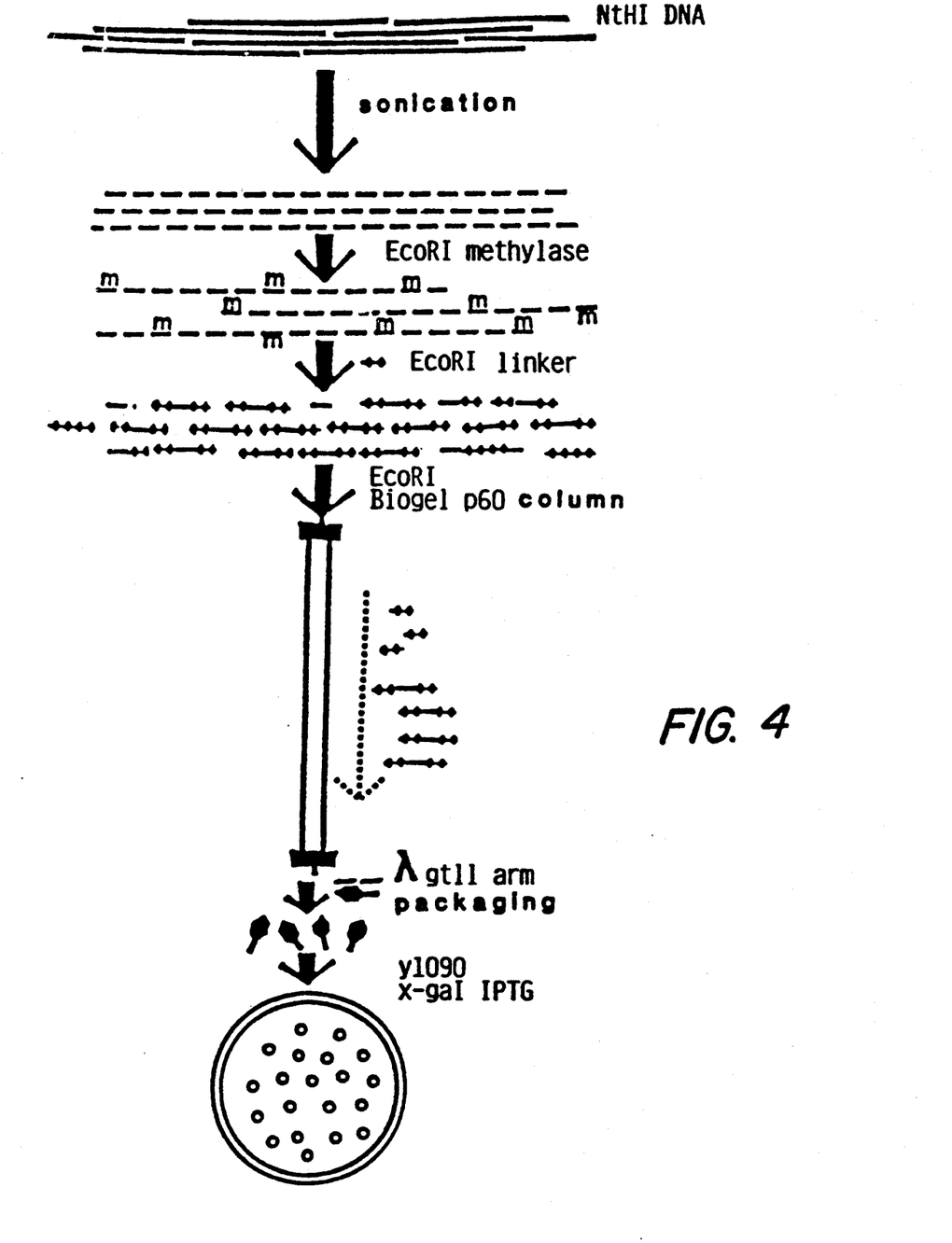

The strategies for the construction of the library, depicted in FIG. 4, were essentially those described by Young and Davis, 1985, Vol. 7, pp 29–41, Genetic Engineering, Plenum Press, N.Y. *Haemophilus influenzae* 1479 DNA was sheared by sonication with one 10 second burst (output control setting at 2) to an average length of 2–4 kilobase pairs (kb). The degree of shear was monitored by agarose gel electrophoresis. The Eco R1 sites of 50 ug of this sheared DNA were methylated using Eco R methylase. The ends of the methylated DNA were made flush by the addition of Klenow polymerase and deoxynucleotide triphosphates. Following this reaction and the addition of sodium acetate to a concentration of 0.3M, the DNA was precipitated. After centrifugation, the pellet was resuspended in Tris-EDTA buffer. The DNA was then ligated to Eco R1 linkers (Bethesda Research Laboratories, Bethesda, Md.) that had been phosphorylated. The ligation reaction was terminated by heating the mixture to 70 degrees C and then the excess Eco R1 linkers were digested using an excess of Eco R1. The methylated *Haemophilus influenzae* 1479 DNA blunt end-ligated to Eco R1 linkers was purified from excess linkers by passage over a gel filtration column (Biogel P60, BIO RAD laboratories, Richmond, Calif.) using a column buffer containing 10 mM Tris pH 7.5, 100 mM NaCl, 1 mM EDTA. Fractions were monitored by $A_{280}$ and agarose gel electrophoresis. Fractions containing DNA of desired size range were pooled, and precipitated. The DNA was pelleted by centrifugation and resuspended in 4 ul of Tris-EDTA buffer. The DNA was ligated to 3 ug of dephosphorylated lambda gt11 arms (STRATA-GENE Cloning Systems, San Dieto, Calif.) in a total reaction volume of 10 ul. The ligation mixture was packaged using two packaging extracts according to the directions of the manufacturer (Gigapack TM, STRATAGENE Cloning Systems). Packaged phage were plated on *E. coli* strain y1090 to determine the titer of plaque forming units and to determine the non-recombinant background by growth with IPTG and X-gal on LB+AMP plates. The library contains approximately 1.5X106 independent recombinant clones with a background of less than or equal to 5%.

Screening the library

Figure 5:
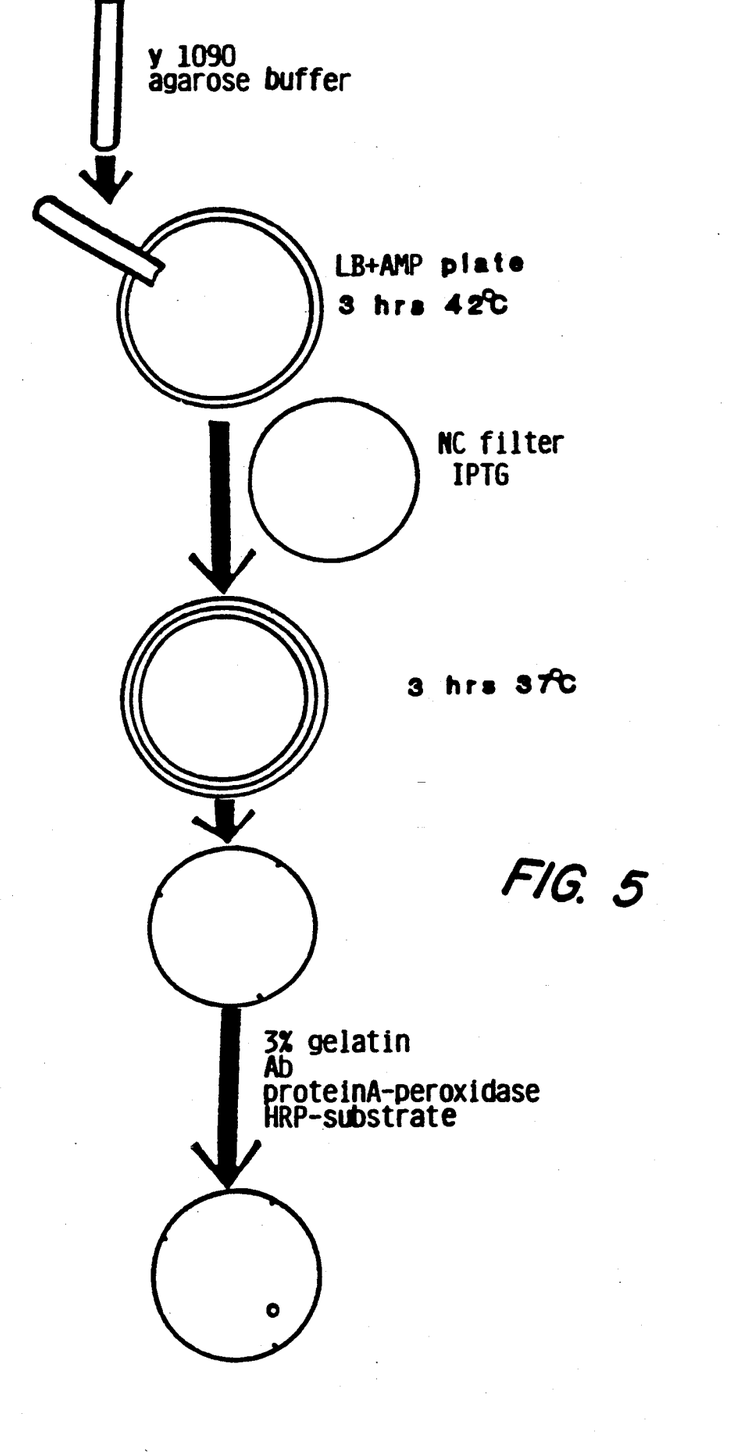

FIG. 5 depicts the methods used in screening. A portion of the y1090 plating stock, 0.2 ml of a y1090 pellet resuspended in 10 mM $MgSO_4$, was infected with $1.5 \times 10^3$ plaque forming units (pfu) of the lambda gt11 library for each 85 mm plate. Following the adsorption incubation, the cells were mixed with LB-agarose buffer, poured and spread evenly onto an LB+AMP plate. The plates were then incubated at 42 degrees C. for 3 hours. Each plate was then overlaid with a dry nitrocellulose filter disk which had been saturated previously in 10 mM IPTG. The plates were then incubated for 3 hours at 37 degrees C. Before removing the filters, the orientation was marked and the filters and respective plates were labelled. The filters were rinsed briefly with buffer A (0.01M Tris, 0.15M NaCl, pH 7.4) and placed in 3% gelatin in buffer A for 1 hour. After the filters were rinsed again with buffer A, they were incubated in a screening mixture of antibodies overnight at room temperature. The screening mixture was buffer A containing 7F3 ascites fluid, at titers of 1:1000. The monoclonal antibody used shared no crossreactivity with the *E. coli* host strains while anti-1808 antiserum required a working dilution of 1:10,000 to maintain sensitivity and specificity. The filters were rinsed with buffer A and placed in a 1:3000 dilution of protein A-peroxidase conjugate and shaken for 1 hour at room temperature. The filters were again rinsed with buffer A, then immersed in horseradish peroxidase color development solution (0.15% $H_2O_2$; BIO RAD, Richmond, Calif.) for 45 minutes. Plaques that appeared positive were removed from their respective plates, resuspended in 500 μls of SM buffer, and rescreened. Plaques that were positive in the rescreening were then rescreened again but against the individual antibodies rather than the screening mixture.

Western blot analysis

The *Haemophilus influenza* control, y1090 recombinants, and the molecular weight standards were prepared by heating at 100 degrees C. for 5 minutes in a sample buffer containing 0.06M Tris pH 6.8, 1.2% SDS, 5% beta-mercaptoethanol, 11.9% glycerol and 0.003% bromophenol blue. The preparations were subjected to SDS-PAGE on a 15% separating gel. Gels were placed on a nitrocellulose sheet which had been previously boiled in distilled water and immersed in a 0.3M sodium citrate, 3M NaCl solution. Electrophoretic transfer was done using a Transphor ® electrophoresis unit (Hoefer Scientific Instruments, San Francisco, Calif.) at 50 volts for 90 minutes, in a buffer of 0.025M Tris, pH 8.3, 0.192M glycine and 20% methanol. The blocking, with subsequent additions of antibody, conjugate, and substrate development was performed in the same manner as described in the plaque screening.

Subcloning into a plasmid vector

A strategy was devised to facilitate sequencing. The DNA insert (which consists of 867 residues), of a recombinant phage expressing P6 epitopes (as determined by screening), was subcloned into a plasmid vector. pUC18 was chosen as the plasmid vector for subcloning for several reasons including a means of selection, an inducible promotor, and an Eco R1 restriction site, features shared by phage cloning vector lambda gt11. The DNA of a recombinant phage was restricted with Eco R1 and then ligated to pUC18 which had been restricted with Eco R1 and dephosphorylated using calf intestinal alkaline phosphatase. The ligation mixture was used to transform competent E. coli strain JM 83. Transformants were selected for by growth on LB+AMP plates overlaid with IPTG and X-gal. White colonies, thought to represent JM 83 containing a plasmid plus insert, were individually picked and transferred to wells of microtiter plates containing L-broth-+AMP+10% glycerol. The plates were incubated overnight at 37 degrees C. A comb device was used to innoculate from the microtiter plates onto nitrocellulose sheets, previously immersed in IPTG, overlaying LB+AMP plates. The plates were incubated overnight at 37 degrees C., and then the nitrocellulose sheets were removed. The nitrocellulose was hung for 15 minutes in a chamber containing chloroform vapors to lyse the colonies, blocked in 3% gelatin containing 40 µg/ml lysozyme and screened in the same way as the genomic library.

Results

Screening the genomic library and characterization of recombinants

Approximately 45,000 plaques were screened, the remainder of the unamplified library being frozen in aliquots at −70 degrees C. in 7% DMSO. Four reactive clones, designated as lambda gt11-*Haemophilus influenzae* 1479 clones O, P, 8, and 10, were found. Efforts focused on clones O and P since they appear to express gene products that are in larger quantities than 8 or 10 and/or more closely resemble the conformation of the native protein, P6.

Plates containing clones O and P were carefully scraped to harvest protein for Western blot analysis. Western blots show that both clones O and P produce a protein that is the same or similar in size to native P6. However, clone O produces the protein in larger quantities when compared to clone P. Therefore, clone O was selected as the recombinant phage for the source of DNA to subclone into a plasmid vector.

Subcloning into a plasmid vector and characterization of the transformant

One thousand transformants, from the same transformation, were screened before one, 7-9B, was found to be positive. To make certain that 7-9B was in pure culture, positive colonies were picked, passaged and rescreened. Western blots of 7-9B grown on plates and in broth show that this recombinant also produces a gene product that is of an apparent molecular weight equal or similar to native P6. The recombinant plasmid pBUD1 isolated from 7-9B, was restricted using Eco R1 and subject to agarose gel electrophoresis to determine the insert size. Restriction analysis, reveals the presence of a 2.5 kb DNA insert containing the P6 gene. The 2.5 kb DNA insert was subsequently reduced in size to facilitate sequencing as shown in Table 3(a).

Discussion

Using molecular cloning techniques, we produced both recombinant phages and recombinant plasmid containing the gene encoding *Haemophilus influenzae* 1479 P6, a 16.6K dalton outer membrane protein. The protein can be described by the nucleic acid sequence between nucleic acid 125 and nucleic acid 526, inclusively as shown in Table 3(b). Expression of the gene product by phage clone O and by *E. Coli* transformat 7-9B is independent of induction of the B-galactasidase promoter. This finding, coupled with Western blot analyses revealing apparently no difference in electrophoretic mobilities between the gene products of clone O and recombinant 7-9B, provide evidence for the likelihood that the recombinant gene product is initiated from its own, the P6 gene's, constitutive promoter.

The epitopes of the 16.6K dalton protein are accessible to monoclonal antibody 7F3 on the surface of *E. coli* transformant 7-9B.

In summary, the gene which codes for P6 was cloned into *E. coli* using a phage vector and plasmid vector. The *E. coli* recombinants express the protein on the surface in a form which is fully immunogenic.

Except as otherwise indicated all microbiological strains are generally available. All such strains as described herein are available from Dr. Timothy Murphy, Division of Infectious Diseases, State University of New York Clinical Center, 462 Grider Street, Buffalo, N.Y. 14215. *H. influenzae* strains 3524 (ATCC 53599), 1479 (ATCC 53600), *E. coli* transformant 7-9B (ATCC 67358) and hybridoma 7F3 (HB 9625) have been deposited with the American Type Culture Collection (ATCC) at 12301 Parklawn Drive, Rockville, Md. 20852 in accordance with the Budapest Treaty.

What is claimed is:

1. A composition useful in the therapeutic treatment of disease due to typable or non-typable *Haemophilus influenzae*, said composition comprising purified antiserum which recognizes a *Haemophilus influenzae* outer membrane protein having a molecular size of from about 15,000 to about 17,000 daltons.

2. The composition of claim 1, wherein said antiserum is a monoclonal antibody or binding fragment or portion thereof, which is bactericidal or elicits an immune clearance in the presence of active complement or neutrophils.

3. The composition of claim 1 wherein said outer membrane protein is P6 having a molecular size of about 16,600 daltons and encoded by a gene having a nucleic acid sequence substantially similar to the sequence:

ATG AAC AAA TTT GTT AAA TCA TTA TTA GTT GCA GGT TCT GTA GCT GCA TTA

GCG GCT TGT AGT TCC TCT AAC AAC GAT GCT GCA GGC AAT GGT GCT GCT CAA

ACT TTT GGC GGA TAC TCT GTT GCT GAT CTT CAA CAA CGT TAC AAC ACC GTA

-continued

```
TAT TTT GGT TTT GAT AAA TAC GAC ATC ACC GGT GAA TAC GTT CAA ATC TTA

GAT GCG CAC GCA GCA TAT TTA AAT GCA ACG CCA GCT GCT AAA GTA TTA GTA

GAA GGT AAT ACT GAT GAA CGT GGT ACA CCA GAA TAC AAC ATC GCA TTA GGA

CAA CGT CGT GCA GAT GCA GTT AAA GGT TAT TTA GCA GGT AAA GGT GTT GAT

GCT GGT AAA TTA GGC ACA GTA TCT TAC GGT GAA GAA AAA CCT GCA GTA TTA

GGT CAC GAT GAA GCT GCA TAT TCT AAA AAC CGT CGT GCA GTG TTA GCG TAC

TTA.
```

4. The composition of claim 2, wherein said monoclonal antibody is produced by hybridoma cell line 7F3 having A.T.C.C. Accession No. HB 9625.

5. A method of passively protecting a human against disease caused by typable or non-typable *Haemophilus influenzae* comprising administering an effective dose of the composition according to claims 1, 2, 3, or 4.

6. A method for the detection of *Haemophilus influenzae* in a sample of tissue or body fluids comprising:
 a) obtaining a sample of tissue or body fluids as a source of antigen;
 b) reacting the sample with purified antiserum which comprises an antibody directed to a *Haemophilus influenzae* outer membrane protein having a molecular size of from about 15,000 to about 17,000 daltons; and
 c) assaying for antigen-antibody complexes.

7. The method of claim 6, wherein said outer membrane protein is P6 having a molecular size of about 16,600 daltons and encoded by a gene having a nucleic acid sequence substantially similar to the sequence:

```
ATG AAC AAA TTT GTT AAA TCA TTA TTA GTT GCA GGT TCT GTA GCT GCA TTA

GCG GCT TGT AGT TCC TCT AAC AAC GAT GCT GCA GGC AAT GGT GCT GCT CAA

ACT TTT GGC GGA TAC TCT GTT GCT GAT CTT CAA CAA CGT TAC AAC ACC GTA

TAT TTT GGT TTT GAT AAA TAC GAC ATC ACC GGT GAA TAC GTT CAA ATC TTA

GAT GCG CAC GCA GCA TAT TTA AAT GCA ACG CCA GCT GCT AAA GTA TTA GTA

GAA GGT AAT ACT GAT GAA CGT GGT ACA CCA GAA TAC AAC ATC GCA TTA GGA

CAA CGT CGT GCA GAT GCA GTT AAA GGT TAT TTA GCA GGT AAA GGT GTT GAT

GCT GGT AAA TTA GGC ACA GTA TCT TAC GGT GAA GAA AAA CCT GCA GTA TTA

GGT CAC GAT GAA GCT GCA TAT TCT AAA AAC CGT CGT GCA GTG TTA GCG TAC

TTA.
```

8. The method of claim 6, wherein said antiserum is a monoclonal antibody.

9. The method of claim 8, wherein said monoclonal antibody recognizes an antigenic determinant that is specific for typable and non-typable *Haemophilus influenzae*.

10. The method of claim 9, wherein said monoclonal antibody is produced by hybridoma cell line 7F3 having ATCC Accession No. HB 9625.

11. A method for the detection of *Haemophilus influenzae* in a sample of tissue or body fluids comprising:
 a) obtaining a sample of tissue or body fluids for use as a source of antibody directed to a *Haemophilus influenzae* outer membrane protein having a molecular size from about 15,000 to 17,000 daltons;
 b) reacting said sample with an antigen comprised of the outer membrane protein of a) or a portion thereof; and
 c) assaying for antigen-antibody complexes which indicates evidence of infection by *Haemophilus influenzae*.

12. The method of claim 11, wherein said outer membrane protein is P6 having a molecular size of about 16,600 daltons and encoded by a gene having a nucleic acid sequence substantially similar to the sequence:

```
ATG AAC AAA TTT GTT AAA TCA TTA TTA GTT GCA GGT TCT GTA GCT GCA TTA

GCG GCT TGT AGT TCC TCT AAC AAC GAT GCT GCA GGC AAT GGT GCT GCT CAA

ACT TTT GGC GGA TAC TCT GTT GCT GAT CTT CAA CAA CGT TAC AAC ACC GTA

TAT TTT GGT TTT GAT AAA TAC GAC ATC ACC GGT GAA TAC GTT CAA ATC TTA

GAT GCG CAC GCA GCA TAT TTA AAT GCA ACG CCA GCT GCT AAA GTA TTA GTA

GAA GGT AAT ACT GAT GAA CGT GGT ACA CCA GAA TAC AAC ATC GCA TTA GGA

CAA CGT CGT GCA GAT GCA GTT AAA GGT TAT TTA GCA GGT AAA GGT GTT GAT

GCT GGT AAA TTA GGC ACA GTA TCT TAC GGT GAA GAA AAA CCT GCA GTA TTA
```

```
GGT CAC GAT GAA GCT GCA TAT TCT AAA AAC CGT CGT GCA GTG TTA GCG TAC
TTA.
```

13. The method of claim 11, wherein said assay is selected from the group consisting of enzyme-immunoassay, enzyme-linked immunosorbent assay, radioimmunoassay, agglutination assay, immunofluorescence assay, or immunoprecipitin assay.

14. A method for the detection of *Haemophilus influenzae* comprising:
   a) obtaining a sample of tissue, body fluid or secretion;
   b) reacting the sample with a probe comprised of a nucleotide sequence synthesized to correspond to a portion of a gene encoding a *Haemophilus influenzae* outer membrane protein having a molecular size of from about 15,000 to about 17,000 daltons;
   c) detecting interaction between the sample and the probe, said interaction being between the genetic material of *Haemophilus influnzae* and the probe.

15. The method of claim 14, wherein said gene encodes P6 having a molecular size of about 16,600 daltons and encoded by a nucleic acid sequence substantially similar to the sequence, or a portion thereof:

```
ATG AAC AAA TTT GTT AAA TCA TTA TTA GTT GCA GGT TCT GTA GCT GCA TTA
GCG GCT TGT AGT TCC TCT AAC AAC GAT GCT GCA GGC AAT GGT GCT GCT CAA
ACT TTT GGC GGA TAC TCT GTT GCT GAT CTT CAA CAA CGT TAC AAC ACC GTA
TAT TTT GGT TTT GAT AAA TAC GAC ATC ACC GGT GAA TAC GTT CAA ATC TTA
GAT GCG CAC GCA GCA TAT TTA AAT GCA ACG CCA GCT GCT AAA GTA TTA GTA
GAA GGT AAT ACT GAT GAA CGT GGT ACA CCA GAA TAC AAC ATC GCA TTA GGA
CAA CGT CGT GCA GAT GCA GTT AAA GGT TAT TTA GCA GGT AAA GGT GTT GAT
GCT GGT AAA TTA GGC ACA GTA TCT TAC GGT GAA GAA AAA CCT GCA GTA TTA
GGT CAC GAT GAA GCT GCA TAT TCT AAA AAC CGT CGT GCA GTG TTA GCG TAC
TTA.
```

16. The method of claim 15, wherein said probe is comprised of a nucleotide sequence corresponding to a nucleic acid sequence capable of specifically binding to the P6 gene of *Haemophilus influenzae*.

17. The method of claim 16, wherein the probe is labelled with a diagnostically recognizable marker selected from the group consisting of a radioactive marker, enzyme marker, fluorescent marker or a chemical marker.

18. A vaccine formulation comprising an immunogenic *Haemophilus influenzae* outer membrane protein having a molecular size of from about 15,000 to about 17,000 daltons, or an immunogenic peptide thereof.

19. The vaccine formulation of claim 18, further mixed with a pharmaceutical carrier.

20. The vaccine formulation of claim 18, wherein the outer membrane protein is P6 having a molecular size of about 16,600 daltons and encoded by a nucleic acid sequence substantially similar to the sequence:

```
ATG AAC AAA TTT GTT AAA TCA TTA TTA GTT GCA GGT TCT GTA GCT GCA TTA
GCG GCT TGT AGT TCC TCT AAC AAC GAT GCT GCA GGC AAT GGT GCT GCT CAA
ACT TTT GGC GGA TAC TCT GTT GCT GAT CTT CAA CAA CGT TAC AAC ACC GTA
TAT TTT GGT TTT GAT AAA TAC GAC ATC ACC GGT GAA TAC GTT CAA ATC TTA
GAT GCG CAC GCA GCA TAT TTA AAT GCA ACG CCA GCT GCT AAA GTA TTA GTA
GAA GGT AAT ACT GAT GAA CGT GGT ACA CCA GAA TAC AAC ATC GCA TTA GGA
CAA CGT CGT GCA GAT GCA GTT AAA GGT TAT TTA GCA GGT AAA GGT GTT GAT
GCT GGT AAA TTA GGC ACA GTA TCT TAC GGT GAA GAA AAA CCT GCA GTA TTA
GGT CAC GAT GAA GCT GCA TAT TCT AAA AAC CGT CGT GCA GTG TTA GCG TAC
TTA.
```

21. The composition of claim 18, wherein the immunogenic peptide represents a portion of outer membrane protein P6 which is conserved among strains of *Haemophilus influenzae*.

22. The composition of claim 21, wherein the amino acid sequence of the immunogenic peptide comprises the epitope recognized by the monoclonal antibody produced by hybridoma 7F3.

23. A method for protecting a human against disease caused by typable or non-typable *Haemophilus influenzae* comprising administering an effective dose of the vaccine according to claims 18, 19, or 21 or 22.

24. A method for protecting a human against disease caused by typable or non-typable *Haemophilus influen-* zae comprising administering an effective dose of a vaccine consisting of a viral or bacterial agent which has been genetically engineered to include the nucleic acid sequence of the gene encoding P6, or an effective portion thereof.

25. The method of claim 24, wherein said nucleic acid sequence comprises:

ATG AAC AAA TTT GTT AAA TCA TTA TTA GTT GCA GGT TCT GTA GCT GCA TTA

GCG GCT TGT AGT TCC TCT AAC AAC GAT GCT GCA GGC AAT GGT GCT GCT CAA

ACT TTT GGC GGA TAC TCT GTT GCT GAT CTT CAA CAA CGT TAC AAC ACC GTA

TAT TTT GGT TTT GAT AAA TAC GAC ATC ACC GGT GAA TAC GTT CAA ATC TTA

GAT GCG CAC GCA GCA TAT TTA AAT GCA ACG CCA GCT GCT AAA GTA TTA GTA

GAA GGT AAT ACT GAT GAA CGT GGT ACA CCA GAA TAC AAC ATC GCA TTA GGA

CAA CGT CGT GCA GAT GCA GTT AAA GGT TAT TTA GCA GGT AAA GGT GTT GAT

GCT GGT AAA TTA GGC ACA GTA TCT TAC GGT GAA GAA AAA CCT GCA GTA TTA

GGT CAC GAT GAA GCT GCA TAT TCT AAA AAC CGT CGT GCA GTG TTA GCG TAC

TTA.

* * * * *